United States Patent
Moore, Jr. et al.

(10) Patent No.: US 6,306,441 B1
(45) Date of Patent: *Oct. 23, 2001

(54) CONCENTRATED AQUEOUS BROMINE SOLUTIONS AND THEIR PREPARATION

(75) Inventors: Robert M. Moore, Jr.; R. Woodrow Wilson, Jr., both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,025

(22) Filed: Nov. 17, 1999

Related U.S. Application Data

(63) Continuation-in-part of application No. 09/088,300, filed on Jun. 1, 1998, now Pat. No. 6,068,861.

(51) Int. Cl.⁷ .......................... A01N 59/02; A01N 39/00; A01N 59/08; A01N 59/00
(52) U.S. Cl. .......................... 424/703; 424/615; 424/665; 424/722; 424/723
(58) Field of Search .................. 424/703, 615, 424/665, 722, 723

(56) References Cited

U.S. PATENT DOCUMENTS

| | | | |
|---|---|---|---|
| 3,152,073 | 10/1964 | Morton | 210/62 |
| 3,170,883 | 2/1965 | Owen et al. | 252/187 |
| 3,308,062 | 3/1967 | Gunther | 210/58 |
| 3,328,294 | 6/1967 | Self et al. | 210/62 |
| 3,558,503 | 1/1971 | Goodenough et al. | 252/187 |
| 3,589,859 | 6/1971 | Foroulis | 21/2.7 |
| 3,711,246 | 1/1973 | Foroulis | 21/2.7 |
| 3,749,672 | 7/1973 | Golton et al. | 252/95 |
| 3,767,586 | 10/1973 | Rutkiewic | 252/187 H |
| 4,032,460 | 6/1977 | Zilch et al. | 252/8.55 B |
| 4,237,090 | 12/1980 | DeMonbrun et al. | 422/13 |
| 4,295,932 | 10/1981 | Pocius | 162/161 |
| 4,382,799 | 5/1983 | Davis et al. | 8/107 |
| 4,427,435 | 1/1984 | Lorenz et al. | 71/67 |
| 4,451,376 | 5/1984 | Sharp | 210/701 |
| 4,465,598 | 8/1984 | Darlington et al. | 210/721 |
| 4,476,930 | 10/1984 | Watanabe | 166/279 |
| 4,490,308 | 12/1984 | Fong et al. | 260/513 N |
| 4,539,071 | 9/1985 | Clifford et al. | 162/161 |
| 4,546,156 | 10/1985 | Fong et al. | 526/240 |
| 4,566,973 | 1/1986 | Masler, III et al. | 210/701 |
| 4,595,517 | 6/1986 | Abadi | 252/82 |
| 4,595,691 | 6/1986 | LaMarre et al. | 514/367 |
| 4,604,431 | 8/1986 | Fong et al. | 525/351 |
| 4,642,194 | 2/1987 | Johnson | 210/699 |
| 4,643,835 | 2/1987 | Koeplin-Gall et al. | 210/754 |
| 4,661,503 | 4/1987 | Martin et al. | 517/372 |
| 4,680,339 | 7/1987 | Fong | 525/54.11 |
| 4,680,399 | 7/1987 | Buchardt | 546/139 |
| 4,703,092 | 10/1987 | Fong | 525/351 |
| 4,711,724 | 12/1987 | Johnson | 210/699 |
| 4,752,443 | 6/1988 | Hoots et al. | 422/13 |
| 4,759,852 | 7/1988 | Trulear | 210/699 |
| 4,762,894 | 8/1988 | Fong et al. | 525/344 |
| 4,777,219 | 10/1988 | Fong | 525/329.4 |
| 4,801,388 | 1/1989 | Fong et al. | 210/701 |
| 4,802,990 | 2/1989 | Inskeep, Jr. | 210/699 |
| 4,822,513 | 4/1989 | Corby | 252/106 |
| 4,846,979 | 7/1989 | Hamilton | 210/754 |
| 4,883,600 | 11/1989 | MacDonald et al. | 210/696 |
| 4,886,915 | 12/1989 | Favstritsky | 564/503 |
| 4,898,686 | 2/1990 | Johnson et al. | 252/389.2 |
| 4,906,651 | 3/1990 | Hsu | 514/372 |
| 4,923,634 | 5/1990 | Hoots et al. | 252/389.2 |
| 4,929,424 | 5/1990 | Meier et al. | 422/9 |
| 4,929,425 | 5/1990 | Hoots et al. | 422/13 |
| 4,966,716 | 10/1990 | Favstritsky et al. | 210/755 |
| 4,992,209 | 2/1991 | Smyk et al. | 252/387 |
| 4,995,987 | 2/1991 | Whitekettle et al. | 210/754 |
| 5,034,155 | 7/1991 | Soeder et al. | 252/389.23 |
| 5,035,806 | 7/1991 | Fong et al. | 210/701 |
| 5,047,164 | 9/1991 | Corby | 252/106 |
| 5,055,285 | 10/1991 | Duncan et al. | 423/473 |
| 5,118,426 | 6/1992 | Duncan et al. | 210/721 |
| 5,120,452 | 6/1992 | Ness et al. | 210/754 |
| 5,120,797 | 6/1992 | Fong et al. | 525/329.4 |
| 5,141,652 | 8/1992 | Moore, Jr. et al. | 210/754 |

(List continued on next page.)

FOREIGN PATENT DOCUMENTS

| | | |
|---|---|---|
| 9015780 | 12/1990 | (WO) . |
| 9720546 | 6/1997 | (WO) . |
| 9720909 | 6/1997 | (WO) . |
| 9734827 | 6/1997 | (WO) . |
| 9743392 | 11/1997 | (WO) . |
| 9815609 | 4/1998 | (WO) . |
| 9906320 | 2/1999 | (WO) . |
| 9932596 | 7/1999 | (WO) . |
| 9955627 | 11/1999 | (WO) . |

OTHER PUBLICATIONS

Willard et al., "Elementary Quantitative Analysis", Third Edition, Chapter XIV—Oxidation and Reduction Processes Involving Iodine (Iodometry) 1940, pp. 261–271.

Ault et al., "Infrared and Raman Spectra of the $M^+Cl_3^-$–ion Pairs and Their Chlorine–bromine Counterparts isolated in Argon Matrices", Journal of Chemical Physics, 1967, vol. 64, No. 12, pp. 4853–4859.

*Primary Examiner*—Alton Pryor
(74) *Attorney, Agent, or Firm*—E. E. Spielman, Jr.

(57) ABSTRACT

A concentrated liquid biocide composition is produced by a continuous process. The process comprises continuously feeding into mixing apparatus (i) bromine chloride and (ii) an aqueous solution of alkali metal salt of sulfamic acid. These are proportioned to produce an aqueous product having an active bromine content of at least 100,000 ppm (wt/wt), and an atom ratio of nitrogen to active bromine from (i) and (ii) greater than 0.93:1. The desired product is withdrawn from the mixing apparatus at a rate sufficient to enable the continuous feeding to be maintained. Thus, the withdrawal of the product can be continuous or intermittent, depending upon the type of mixing apparatus being used.

28 Claims, 1 Drawing Sheet

U.S. PATENT DOCUMENTS

| | | | |
|---|---|---|---|
| 5,179,173 | 1/1993 | Fong et al. | 525/329.4 |
| 5,192,459 | 3/1993 | Tell et al. | 252/106 |
| 5,194,238 | 3/1993 | Duncan et al. | 423/473 |
| 5,196,126 | 3/1993 | O'Dowd | 210/754 |
| 5,202,047 | 4/1993 | Corby | 252/106 |
| 5,259,985 | 11/1993 | Nakanishi et al. | 252/180 |
| 5,264,136 | 11/1993 | Howarth et al. | 210/754 |
| 5,389,384 | 2/1995 | Jooste | 424/661 |
| 5,414,652 | 5/1995 | Mieda et al. | 365/122 |
| 5,424,032 | 6/1995 | Christensen et al. | 422/14 |
| 5,443,849 | 8/1995 | Corby | 424/667 |
| 5,464,636 | 11/1995 | Hight et al. | 424/661 |
| 5,525,241 | 6/1996 | Clavin et al. | 210/753 |
| 5,527,547 | 6/1996 | Hight et al. | 424/661 |
| 5,589,106 | 12/1996 | Shim et al. | 252/387 |
| 5,607,619 | 3/1997 | Dadgar et al. | 252/187.2 |
| 5,679,239 | 10/1997 | Blum et al. | 205/556 |
| 5,683,654 | 11/1997 | Dallmier et al. | 422/14 |
| 5,795,487 | 8/1998 | Dallmier et al. | 210/754 |
| 5,900,512 | 5/1999 | Elnagar et al. | 568/14 |
| 5,922,745 | 7/1999 | McCarthy et al. | 514/372 |
| 5,942,126 | 8/1999 | Dallmier et al. | 210/756 |
| 6,007,726 | 12/1999 | Yang et al. | 210/752 |
| 6,068,861 * | 5/2000 | Moore et al. | 424/703 |
| 6,110,387 * | 8/2000 | Choudhury et al. | 210/752 |
| 6,123,870 | 9/2000 | Yang et al. | 252/186.1 |
| 6,156,229 | 12/2000 | Yang et al. | 252/186.1 |

* cited by examiner

CONCENTRATED AQUEOUS BROMINE SOLUTIONS AND THEIR PREPARATION

REFERENCE TO RELATED APPLICATIONS

This is a continuation-in-part of prior commonly-owned Application Ser. No. 09/088,300, filed Jun. 1, 1998, now U.S. Pat. No. 6,068,861.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to $HOBr/OBr^-$. This activated solution is then introduced directly into the water system to be treated. The feeding of the two liquids in this fashion is necessary because the $HOBr/OBr^-$ mixture is unstable and has to be generated on-site just prior to its introduction to the water. Furthermore, the feeding, and metering of two liquids is cumbersome, especially as the system has to be designed to allow time for the activation of bromide ion to occur. Consequently many biocide users have expressed the need for a single-feed, bromine-based biocide. Molecular bromine chloride is deemed to meet these demands. It is a liquid at room temperature and can be fed directly to the water system, where immediate hydrolysis occurs to yield HOBr.

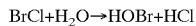

$$BrCl+H_2O \rightarrow HOBr+HCl$$

Bromine chloride is a fuming, red liquid or gas, with a boiling point of 5° C., and a vapor pressure of 1800 mm at 25° C. It corrodes most metals in the presence of water.

It can be seen that certain characteristics of bromine chloride—especially its corrosiveness, high vapor pressure and fuming tendencies—necessitate care and skill in its handling and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

The commonly-owned copending continued prosecution application referred to at the out-set describes, inter alia, a new process of forming concentrated aqueous solutions of biocidally active bromine and in so doing, provides novel and eminently useful concentrated aqueous biocidal solutions of bromine chloride. Such solutions are formed by a process which comprises mixing (a) bromine chloride with (b) an aqueous solution of alkali metal salt of sulfamic acid (preferably the sodium salt), the resulting solution having a pH of at least about 7, e.g., in the range of 7 to about 14, and preferably above 7 to about 14. Most preferably the pH is in the range of about 13.0 to about 13.7. The amounts of (a) and (b) used are such that (i) the content of active bromine in the solution is at least 100,000 ppm (wt/wt) and (ii) the atom ratio of nitrogen to active bromine from (a) and (b) is greater than 0.93, and preferably is greater than 1.

SUMMARY OF THE INVENTION

One objective of this invention is to enable the process of the commonly-owned copending application to be carried out not only in a commercially-feasible manner, but in addition, in an exceptionally efficient manner on a continuous basis. Other objectives may appear hereinafter.

In one of its embodiments this invention provides a process of producing a concentrated liquid biocide composition which process comprises:

A) continuously feeding into mixing apparatus (i) bromine chloride and (ii) an aqueous solution of alkali metal salt of sulfamic acid (preferably a sodium salt of sulfamic acid), proportioned to produce an aqueous product having an active bromine content of at least 100,000 ppm (wt/wt), and an atom ratio of nitrogen to active bromine from (i) and (ii) greater than 0.93 (preferably greater than 1); and B) withdrawing said product from said mixing apparatus at a rate sufficient to enable the continuous feeding in A) to be maintained.

In other embodiments, the bromine chloride is continuously formed from equimolar amounts of bromine and chlorine, and at least a portion of the bromine chloride being continuously produced is used as the continuous feed of bromine chloride in step A) above. Thus in plant facilities where bromine chloride is required or desired for use(s) in addition to that required to maintain the continuous feed of (i) in step A) above, the continuous production of the bromine chloride can be scaled up to serve all such uses.

A preferred embodiment includes, in addition to steps A) and B) as described above, the following concurrent operation, namely, continuously, but alternately, withdrawing from at least one and then from at least one other of at least two reaction vessels, an aqueous solution of alkali metal salt of sulfamic acid at a rate that maintains said stream of (ii) in A), and during the time the solution is being withdrawn from said at least one of at least two reaction vessels, forming additional aqueous solution of alkali metal salt of sulfamic acid in said at least one other of at least two reaction vessels from which solution is not then being withdrawn. In this way, aqueous alkali metal sulfamate solution can be continuously withdrawn from one or more tanks ("Tank(s) I") to serve as the continuous feed of (ii) in A), while forming more of such solution in one or more other tanks ("Tank(s) II"), so that when Tank(s) I is/are depleted, the system is switched to Tank(s) II which then serve(s) as the supply for the continuous feed of (ii) in A) until depleted, and by that time more of such solution has been formed in Tank(s) I. Thus by alternating the supply and the production from one tank (or group of tanks) to another tank (or group of tanks) and switching back and forth between the filled tanks as the supply, the continuous feed of the aqueous alkali metal sulfamate solution can be maintained without material interruption. A particularly preferred embodiment of this invention is a process which comprises:

A) continuously feeding into mixing apparatus (i) a bromine chloride stream identified below in C), and (ii) a separate feed stream of an aqueous solution of alkali metal salt of sulfamic acid identified below in D), in proportions that produce an aqueous product having an active bromine content of at least 100,000 ppm (wt/wt), and an atom ratio of nitrogen to active bromine from (i) and (ii) greater than 0.93;

B) withdrawing the aqueous product from the mixing apparatus at a rate sufficient to enable the continuous feeding in A) to be maintained;

C) continuously contacting bromine and chlorine in a vessel in equimolar quantities such that bromine chloride is produced, and continuously withdrawing from this vessel a bromine chloride product stream at a rate that maintains the feed of (i) in A), at least a portion of this bromine chloride product stream constituting the bromine chloride stream (i) of A); and D) continuously, but alternately, withdrawing from at least one and then from at least one other of at least two reaction vessels, an aqueous solution of alkali metal salt of sulfamic acid at a rate that maintains the stream of (ii) in A), and during the time the solution is being withdrawn from at least one of the reaction vessels, forming additional aqueous solution of alkali metal salt of sulfamic acid in at least one other of the reaction vessels from which solution is not then being withdrawn.

The above and other embodiments and features of this invention will be still further apparent from the ensuing description, the accompanying drawing, and/or the appended claims.

FURTHER DETAILED DESCRIPTION OF THE INVENTION

Figure 1:
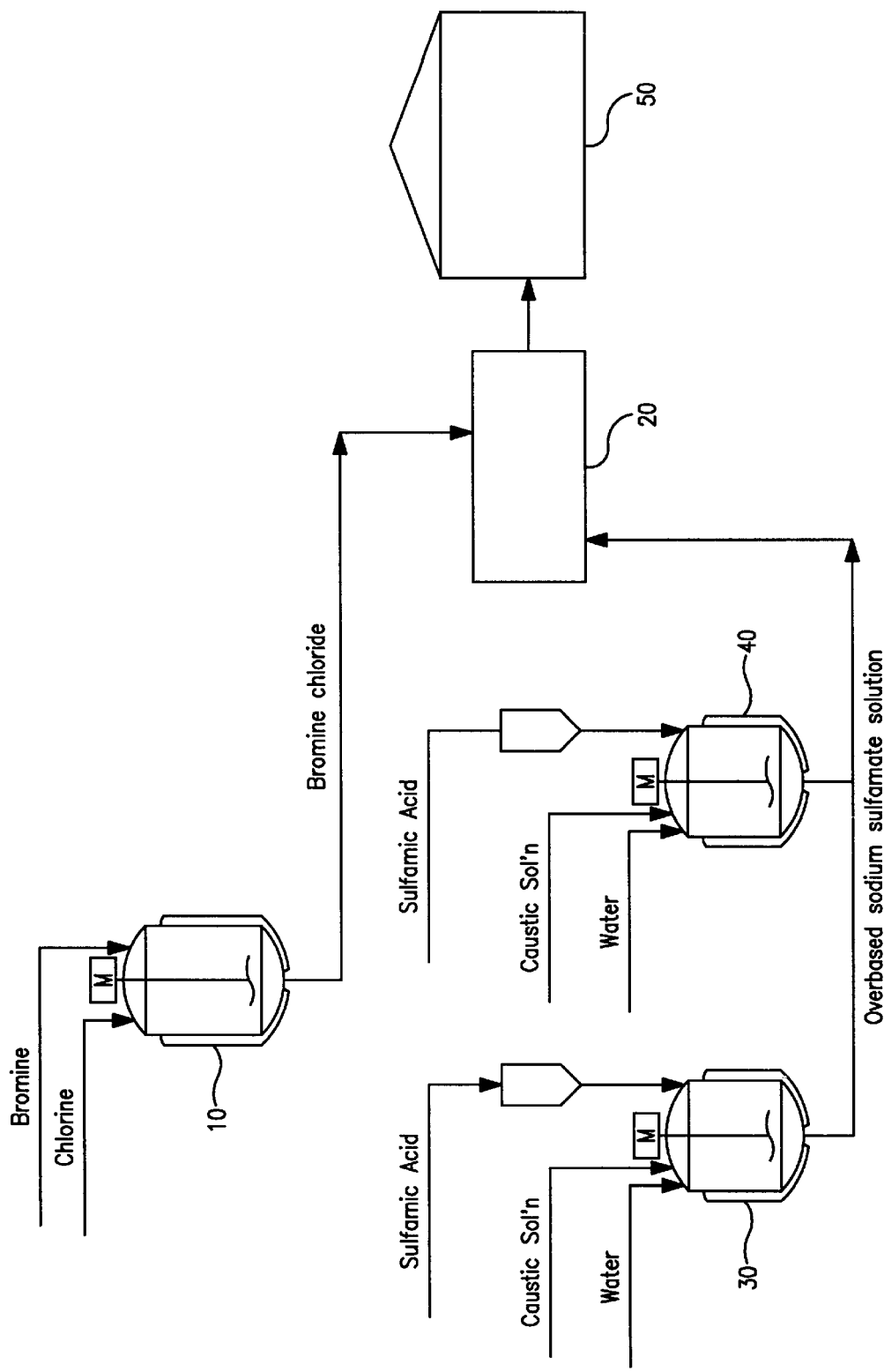
FIG. 1 is a schematic flow diagram of a plant layout suitable for the practice of the continuous processes of this invention.

Various types of mixing apparatus can be used in the practice of this invention. In one preferred embodiment the mixing apparatus comprises a static mixer. The static mixer can be of any suitable design and configuration as long as it is capable of continuously receiving the continuous feed streams of bromine chloride and aqueous alkali metal sulfamate solution, and continuously discharging a mixture formed from these feed streams that is substantially uniform in composition and thus satisfies product specifications.

Another preferred mixing apparatus comprises a vessel equipped with a mechanical stirrer. In this case, the vessel continuously receives the continuous feed streams of bromine chloride and aqueous alkali metal sulfamate solution, and either continuously or intermittently discharges a substantially uniform mixture formed from these feed streams. The mechanical stirrer can be programmed to operate continuously or intermittently as long as the discharge from the vessel is constantly substantially uniform in composition. Thus if the discharge from the vessel is intermittent, the incoming continuous feeds are preferably agitated during at least most of the time the vessel is filling up to a predetermined volume at which point the contents of the vessel are discharged more rapidly than the total incoming feeds until the vessel reaches a predetermined low volume, at which point the discharge is discontinued so that the vessel begins to fill up again. On the other hand, if the discharge is continuous, the system is designed and constructed such that the total incoming volume to the vessel and the concurrent outgoing volume from the vessel remain equal and so that the vessel continuously contains a predetermined volume of contents which are being mixed by the mechanical stirrer. In such case, the stirrer preferably is operated continuously.

The bromine chloride can be preformed bromine chloride maintained and sourced from storage tanks. Preferably however the bromine chloride is concurrently being prepared in a suitable corrosion-resistant reaction vessel on a continuous basis from equimolar amounts of bromine and chlorine. As indicated above, the amount of bromine chloride being continuously produced can equal the amount of bromine chloride being continuously fed to the mixing apparatus, when there is no other need or desire for additional amounts of bromine chloride. But if there are other such needs or desires, the amount of bromine chloride production can be scaled up to meet such needs or desires. The bromine chloride is typically formed by contacting the reactants in equimolar quantities and maintaining the temperature of the mixture in the range of about 10 to about 50° C.

Use of bromine chloride as the source of the active bromine in the concentrated stabilized liquid biocide formulations produced pursuant to this invention is highly advantageous. When such biocidal formulations are used to treat water, all of the bromine of the bromine chloride is made available as active bromine in the resulting highly dilute solution. In other words, the chlorine of the bromine chloride is converted in the process to dissolved alkali metal chloride salt, thereby liberating the bromine as the active bromine content of the biocidal composition. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

The aqueous solution of alkali metal salt of sulfamic acid (alkali metal sulfamate) can be preformed and sourced from storage vessels in supplying the other continuous feed to the mixing apparatus. However it is preferred to concurrently produce such aqueous solution at a rate sufficient to at least continuously supply the amount required to maintain such continuous feed to the mixing apparatus. If there are other needs or desires for such aqueous solution, the amount of solution produced can be scaled up to satisfy such needs or desires.

It is possible to form the aqueous solution of alkali metal salt of sulfamic acid by mixing dry sulfamic acid with a dry water-soluble the alkali metal base also in the dry state, and then mix the resultant dry mixture of solids with water. It is also possible to form the aqueous solution of alkali metal salt of sulfamic acid by mixing dry sulfamic acid with an aqueous solution of alkali metal base. However, the aqueous solution of alkali metal sulfamate is preferably formed by mixing together a slurry of sulfamic acid in water and a solution of the water-soluble alkali metal base.

Any water-soluble inorganic alkali metal base can be used in forming the aqueous solution of alkali metal sulfamate. Examples of such bases include the oxides, hydroxides, carbonates, bicarbonates, acetates, sulfates, and the like. While a water-soluble basic salt or oxide of any alkali metal can be used, the sodium salts or oxides are preferred. However potassium salts or oxides are also very useful. Mixtures of two or more water-soluble sodium bases, mixtures of two or more water-soluble potassium bases, or mixtures of one or more water-soluble sodium bases and one or more water-soluble potassium bases can be used. Highly preferred are aqueous sodium hydroxide solutions which can be formed from sodium oxide or sodium hydroxide. Typically the aqueous solution will contain in the range of about 10 to about 55 wt % of the alkali metal base, but any concentration of such base that enables the formation of an aqueous bromine chloride solution meeting the pH requirements of this invention can be employed.

Besides having an active bromine content of at least 100,000 ppm (wt/wt), the concentrated solution emanating from the mixing apparatus preferably has a pH of at least 7, e.g., a pH in the range of 7 to about 14, and preferably above 7 to about 14. Most preferably this solution is a solution with a pH in the range of about 13.0 to about 13.7. The pH of the concentrated is typically governed by the pH of the aqueous alkali metal sulfamate solution used as the feed to the mixing apparatus.

It is possible for the solution emanating from the mixing apparatus to have a pH with a numerical value lower than desired, and to feed additional base into the solution after it has left the mixing apparatus to raise the pH to the desired numerical value. Alternatively, a separate aqueous solution of alkali metal base can be fed concurrently and continuously to the mixing apparatus to achieve a more alkaline (basic) concentrated product solution leaving the mixing apparatus. Neither of these latter two procedures is a preferred way to operate, however.

Therefore, in the preferred operating modes the proportions of the bromine chloride and the aqueous alkali metal sulfamate solution continuous feed streams to the mixing apparatus are such that (i) the content of active bromine in the resulting product solution is at least 100,000 ppm (wt/wt) and (ii) the atom ratio of nitrogen to active bromine from these feed streams is greater than 0.93, and more preferably in the range of about 1.0 to about 1.4.

By utilizing bromine chloride with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to Goodenough, et al. U.S. Pat. No. 3,558,503. Moreover, even at the high levels of active bromine that exist in the compositions of this invention, it has been found possible to provide biocidal compositions that maintain these high levels of active bromine for at least a two-month period, and that do not exhibit a visible or offensive vapor or odor during this period.

In each of the embodiments of this invention the operation is preferably conducted such that the concentrated product solution produced in the process has an active bromine content in the range of about 120,000 ppm wt/wt (12 wt %) to about 180,000 ppm wt/wt (18 wt %). Also in each of the embodiments of this invention, the atom ratio of nitrogen to active bromine in the concentrated product solution is preferably at least 1:1, e.g., in the range of about 1.1 to about 1.5. Still higher ratios can be employed, if desired. A particularly preferred atom ratio is from 1.0:1 to 1.4:1.

The processes of this invention are continuous processes and involve continuous feeds to the mixing apparatus. In addition, some embodiments of the invention involve continuous formation of bromine chloride, or continuous contacting of bromine and chlorine to form bromine chloride, or continuous alternate withdrawal of an aqueous solution of alkali metal salt of sulfamic acid from at least one reaction vessel while another quantity of such solution is being formed in at least one other such vessel. In such embodiments the term "continuous" or "continuously" is not meant to exclude interrupted feeds or withdrawals. Generally, if such interruptions occur, they are of short duration and are such as not to materially affect the steady state operation of the overall process, and also are such as not to cause production of a significant quantity of off-specification concentrated product solution. An example of such a slight, non-adverse interruption may occur when switching the flow of aqueous solution of alkali metal salt of sulfamic acid from at least one reaction vessel to another such vessel, an operation which is referred to above as part of a "continuous" feed. As long as such switching operation does not disrupt the operation or result in the formation of a significant quantity of off-specification concentrated product solution, such interruption is acceptable and is within the spirit of the term "continuous". An exception exists where the term "continuous" does not allow for interruption, namely in any case where both continuous and non-continuous (e.g., "intermittent") operation in a given step or operation are both expressly referred to herein. An example of this exception is the embodiment where product is continuously withdrawn from above-referred-to vessel that is equipped with a mechanical stirrer. Such "continuous" withdrawal is not interrupted because in another embodiment expressly referred to herein, the withdrawal of the same product from the same vessel is specifically described as "intermittent". Thus both alternatives (continuous and non-continuous) are expressly referred to in this disclosure.

Reference is now made to the drawing, which is largely self-explanatory. In the plant flow diagram schematically depicted, separate equimolar streams of bromine and chlorine are fed, preferably continuously, into stirred jacketed reactor 10. The contents reactor 10 are typically maintained at a temperature in the range of about −30 to about 30° C. so that bromine chloride is produced, preferably continuously. The bromine chloride is transmitted continuously into mixing apparatus 20. Concurrently sulfamic acid, a 15–25 wt % aqueous solution of sodium hydroxide, and water are charged into either jacketed reactor 30 or jacketed reactor 40, and the resultant mixture therein is agitated and maintained at about 10 to about 50° C. The sulfamic acid and the sodium hydroxide are proportioned to produce in the reactor an aqueous solution of sodium sulfamate having a pH which preferably is in the range of about 13.0 to about 14.0. The reactor 30 or 40 which is not then being used to prepare such aqueous sodium sulfamate solution, contains an identical aqueous solution previously made therein in the same manner. A stream of such aqueous sodium sulfamate solution is continuously withdrawn from reactor 30 or 40 (as the case may be) which contains the previously made solution, and this stream is continuously fed into mixing apparatus 20. The interaction between the bromine chloride and the sodium sulfamate solution tends to be exothermic. Therefore, it is desirable, particularly in large scale facilities, to cool the mixture as it is being formed. The effluent from mixing apparatus 20 is the concentrated stabilized aqueous biocidal formulation. This product solution is transferred from mixing apparatus 20 to a storage tank 50 or equivalent container such as a railcar or tank truck. If mixing apparatus 20 is a static mixer, the effluent from the static mixer is continuously transferred to the storage tank 50. On the other hand, if mixing apparatus 20 is, say, a vessel equipped with a mechanical stirrer, and such vessel is intermittently drained so that its contents oscillate between high and low contents of product solution, the transmission of the product solution from such mixing apparatus 20 to storage tank 50 is intermittent. Means (not shown) such as electrically-operated valves and associated electronics for sensing and signaling when to shut one valve while opening the other are included so that the continuous alternate flow of aqueous sodium sulfamate solution from one and then the other of reactors 30 and 40 to mixing apparatus 20 can be maintained on a continuous basis.

Instead of the separate feeds depicted in the drawing of sulfamic acid, a 15–25 wt % aqueous solution of sodium hydroxide, and water that alternate back and forth between one of reactors 30 and 40 while the other reactor is being drained, separate flows of the aqueous solution of sodium hydroxide and a preformed aqueous slurry of sulfamic can be fed alternately to to these reactors. It may be expected that other variations and details in the depicted schematic plant flow diagram and/or in the mode of operation will now be readily apparent to those of ordinary skill in the art.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing a concentrated liquid biocide composition, which process comprises
    A) continuously feeding into mixing apparatus compounds/liquids consisting essentially of (i) bromine chloride and (ii) an overbased aqueous solution of alkali metal salt of sulfamic acid, proportioned to produce an aqueous product having an active bromine content of at least 100,000 ppm (wt/wt), a pH of at least 7 and an atom ratio of nitrogen to active bromine from (i) and (ii) greater than 0.93:1; and
    B) withdrawing said product from said mixing apparatus at a rate sufficient to enable the continuous feeding in A) to be maintained.

2. A process according to claim 1 wherein (ii) in A) is an overbased aqueous solution of the sodium salt of sulfamic acid, and wherein said atom ratio is at least 1:1.

3. A process according to claim 2 wherein said active bromine content is in the range of about 120,000 ppm (wt/wt) to about 180,000 ppm (wt/wt), and said atom ratio is in the range of 1.0:1 to 1.4:1.

4. A process according to claim 1 wherein said mixing apparatus comprises a static mixer.

5. A process according to claim 1 wherein said mixing apparatus comprises a vessel equipped with a mechanical stirrer.

6. A process according to claim 5 wherein said product is intermittently withdrawn from said vessel.

7. A process according to claim 5 wherein said product is continuously withdrawn from said vessel.

8. A process of producing a concentrated liquid biocide composition, which process comprises
    A) continuously forming bromine chloride from equimolar amounts of bromine and chlorine;
    B) continuously feeding into mixing apparatus compounds/liquids consisting essentially of (i) bromine chloride formed in A) and (ii) an overbased aqueous solution of alkali metal salt of sulfamic acid, in proportions that produce an aqueous product having an active bromine content of at least 100,000 ppm (wt/wt), a pH of at least 7 and an atom ratio of nitrogen to active bromine from (i) and (ii) greater than 0.93:1; and
    C) withdrawing said aqueous product from said mixing apparatus at a rate sufficient to enable the continuous feeding in B) to be maintained.

9. A process according to claim 8 wherein (ii) in B) is an overbased aqueous solution of the sodium salt of sulfamic acid, and wherein said atom ratio is at least 1:1.

10. A process according to claim 9 wherein said active bromine content is in the range of about 120,000 ppm (wt/wt) to about 180,000 ppm (wt/wt), and said atom ratio is in the range of 1.0:1 to 1.4:1.

11. A process according to claim 8 wherein said mixing apparatus comprises a static mixer.

12. A process according to claim 8 wherein said mixing apparatus comprises a vessel equipped with a mechanical stirrer.

13. A process according to claim 12 wherein said product is intermittently withdrawn from said vessel.

14. A process according to claim 12 wherein said product is continuously withdrawn from said vessel.

15. A process of producing a concentrated liquid biocide composition, which process comprises
    A) continuously feeding into mixing apparatus compounds/liquids consisting essentially of (i) a bromine chloride stream hereinafter described in c), and (ii) a separate feed stream of an overbased aqueous solution of alkali metal salt of sulfamic acid, in proportions that produce an aqueous product having an active bromine content of at least 100,000 ppm (wt/wt), a pH of at least 7 and an atom ratio of nitrogen to active bromine from (i) and (ii) greater than 0.93:1;
    B) withdrawing said product from said mixing apparatus at a rate sufficient to enable the continuous feeding in A) to be maintained; and
    C) continuously contacting bromine and chlorine in a vessel in equimolar quantities such that bromine chloride is produced, and continuously withdrawing from said vessel a bromine chloride product stream at a rate that maintains the feed of (i) in A), at least a portion of said bromine chloride product stream constituting the bromine chloride stream (i) of A).

16. A process of producing a concentrated liquid biocide composition, which process comprises.
    A) continuously feeding into mixing apparatus compounds/liquids consisting essentially of (i) a bromine chloride stream, and (ii) a separate feed stream of an overbased aqueous solution of alkali metal salt of sulfamic acid, in proportions that produce an aqueous product having an active bromine content of at least 100,000 ppm (wt/wt), a pH of at least 7 and an atom ratio of nitrogen to active bromine from (i) and (ii) greater than 0.93:1;
    B) withdrawing said product from said mixing apparatus at a rate sufficient to enable the continuous feeding in A) to be maintained; and
    C) continuously, but alternately, withdrawing from at least one and then from at least one other of at least two reaction vessels, an aqueous solution of alkali metal salt of sulfamic acid at a rate that maintains said stream of (ii) in A), and during the time the solution is being withdrawn from said at least one of at least two reaction vessels, forming additional aqueous solution of alkali metal salt of sulfamic acid in said at least one other of at least two reaction vessels from which solution is not then being withdrawn.

17. A process of producing a concentrated liquid biocide composition, which process comprises A) continuously feeding into mixing apparatus compounds/liquids consisting essentially of (i) a bromine chloride stream hereinafter described, and (ii) a separate feed stream of an overbased aqueous solution of alkali metal salt of sulfamic acid, in proportions that produce an aqueous product having an active bromine content of at least 100,000 ppm (wt/wt), a pH of at least 7 and an atom ratio of nitrogen to active bromine from (i) and (ii) greater than 0.93:1;

B) withdrawing said aqueous product from said mixing apparatus at a rate sufficient to enable the continuous feeding in A) to be maintained;

C) continuously contacting bromine and chlorine in a vessel in equimolar quantities such that bromine chloride is produced, and continuously withdrawing from said vessel a bromine chloride product stream at a rate that maintains the feed of (i) in A), at least a portion of said bromine chloride product stream constituting the bromine chloride stream (i) of A); and D) continuously, but alternately, withdrawing from at least one and then from at least one other of at least two reaction vessels, an aqueous solution of alkali metal salt of sulfamic acid at a rate that maintains the stream of (ii) in A), and during the time the solution is being withdrawn from at least one of the reaction vessels, forming additional aqueous solution of alkali metal salt of sulfamic acid in at least one other of the reaction vessels from which solution is not then being withdrawn.

18. A process according to any of claims 15–17 wherein said overbased aqueous solution of alkali metal salt of sulfamic acid is an overbased aqueous solution of the sodium salt of sulfamic acid, and wherein said atom ratio is at least 1:1.

19. A process according to any of claims 15–17 wherein said overbased aqueous solution of alkali metal salt of sulfamic acid is an overbased aqueous solution of the sodium salt of sulfamic acid, wherein said active bromine content is in the range of about 120,000 ppm (wt/wt) to about 180,000 ppm (wt/wt), and wherein said atom ratio is in the range of 1.0:1 to 1.4:1.

20. A process according to any of claims 15–17 wherein said mixing apparatus comprises a static mixer.

21. A process according to any of claims 15–17 wherein said mixing apparatus comprises a vessel equipped with a mechanical stirrer.

22. A process according to claim 21 wherein in B) said aqueous product is intermittently withdrawn from said vessel.

23. A process according to claim 21 wherein in B) said aqueous product is continuously withdrawn from said vessel.

24. A process according to claim 16 or 17 wherein said mixing apparatus comprises a static mixer, and wherein said additional aqueous solution of alkali metal salt of sulfamic acid is formed from an alkali metal base, sulfamic acid, and water.

25. A process according to claim 16 or 17 wherein said mixing apparatus comprises a static mixer, wherein said aqueous solution of alkali metal salt of sulfamic acid is an aqueous solution of sodium sulfamate, and wherein said additional aqueous solution of alkali metal salt of sulfamic acid is formed from a water-soluble sodium base, sulfamic acid, and water.

26. A process according to claim 25 wherein said sodium base is an aqueous solution of sodium hydroxide, and wherein the sodium sulfamate is formed a s an aqueous solution by charging to a reactor (i) an aqueous solution of sodium hydroxide, and (ii) a slurry of sulfamic acid in water, or (iii) separate charge s of sulfamic acid and water, or (iv) both of (ii) and (iii).

27. A process of producing a concentrated liquid biocide composition, which process comprises A) continuously feeding into mixing apparatus compounds/liquids consisting essentially of (i) bromine chloride and (ii) an aqueous solution of alkali metal salt of sulfamic acid, proportioned to produce an aqueous product having an active bromine content of at least 100,000 ppm (wt/wt) and an atom ratio of nitrogen to active bromine from (i) and (ii) greater than 0.93:1;

B) withdrawing said product from said mixing apparatus at a rate sufficient to enable the continuous feeding in A) to be maintained;

C) feeding alkali metal hydroxide into the aqueous product after said product has left the mixing apparatus to raise the pH to a pH of 7 to about 14.

28. A process according to claim 27 wherein said aqueous solution of the salt of sulfamic acid is an overbased aqueous solution of the sodium salt of sulfamic acid.

* * * * *

UNITED STATES PATENT AND TRADEMARK OFFICE
CERTIFICATE OF CORRECTION

PATENT NO. : 6,306,441 B1 Page 1 of 1
DATED : October 23, 2001
INVENTOR(S) : Robert M. Moore, Jr. and R. Woodrow Wilson, Jr.

It is certified that error appears in the above-identified patent and that said Letters Patent is hereby corrected as shown below:

<u>Title page,</u>
Item [56], References Cited, FOREIGN PATENT DOCUMENTS, reads
"9734827    6/1997 (WO)" and should read -- 9734827    9/1997 (WO) --

<u>Column 9,</u>
Line 11, reads "..hereinafter described,…" and should read -- …hereinafter described in C)… --

Signed and Sealed this

Twenty-fourth Day of December, 2002

JAMES E. ROGAN
*Director of the United States Patent and Trademark Office*